(12) United States Patent
Baldi et al.

(10) Patent No.: US 11,434,145 B2
(45) Date of Patent: Sep. 6, 2022

(54) NANO-FUNCTIONALIZED SUPPORT AND PRODUCTION METHOD THEREOF

(71) Applicant: COLOROBBIA CONSULTING S.r.l., Vinci (IT)

(72) Inventors: Giovanni Baldi, Montespertoli (IT); Andrea Cioni, Empoli (IT); Valentina Dami, Larciano (IT); Laura Niccolai, Montelupo Fiorentino (IT); Marco Bitossi, Montelupo Fiorentino (IT)

(73) Assignee: COLOROBBIA CONSULTING S.R.L., Vinci (IT)

( * ) Notice: Subject to any disclaimer, the term of this patent is extended or adjusted under 35 U.S.C. 154(b) by 236 days.

(21) Appl. No.: 16/611,695

(22) PCT Filed: May 9, 2018

(86) PCT No.: PCT/IB2018/053216
§ 371 (c)(1),
(2) Date: Nov. 7, 2019

(87) PCT Pub. No.: WO2018/207107
PCT Pub. Date: Nov. 15, 2018

(65) Prior Publication Data
US 2021/0139341 A1 May 13, 2021

(30) Foreign Application Priority Data

May 10, 2017 (IT) .................. 102017000050577

(51) Int. Cl.
| | |
|---|---|
| *B01J 21/06* | (2006.01) |
| *C01G 23/08* | (2006.01) |
| *B01D 53/86* | (2006.01) |
| *B01J 21/04* | (2006.01) |
| *B01J 27/24* | (2006.01) |
| *B01J 35/00* | (2006.01) |
| *B01J 35/04* | (2006.01) |
| *B01J 37/08* | (2006.01) |
| *B82Y 30/00* | (2011.01) |
| *B82Y 40/00* | (2011.01) |

(52) U.S. Cl.
CPC ......... *C01G 23/08* (2013.01); *B01D 53/8628* (2013.01); *B01J 21/04* (2013.01); *B01J 21/063* (2013.01); *B01J 27/24* (2013.01); *B01J 35/004* (2013.01); *B01J 35/04* (2013.01); *B01J 37/08* (2013.01); *B01D 2255/20707* (2013.01); *B01D 2255/707* (2013.01); *B01D 2255/802* (2013.01); *B01D 2257/404* (2013.01); *B01D 2258/06* (2013.01); *B01D 2259/802* (2013.01); *B82Y 30/00* (2013.01); *B82Y 40/00* (2013.01); *C01P 2002/54* (2013.01)

(58) Field of Classification Search
None
See application file for complete search history.

(56) References Cited

U.S. PATENT DOCUMENTS

| | | | | |
|---|---|---|---|---|
| 2002/0169076 A1* | 11/2002 | Takeshi | ................. | B01J 35/004 |
| | | | | 502/350 |
| 2019/0039047 A1* | 2/2019 | Kimura | ............... | B01J 20/3206 |

FOREIGN PATENT DOCUMENTS

CN 101423250 * 10/2008

OTHER PUBLICATIONS

Tumuluri, Uma et al. "Effect of Surface Structure of TiO2 nanoparticles . . . ". ACS Sustainable CHem. Eng. 5, 9295-9306 (2017). (Year: 2017).*
Liao, Yusen et al. "Efficient CO2 Capture and Photoreduction . . . ". Chem. Eur. J. 20, 10220-10222 (2014). (Year: 2014).*
Cargnello, Mateo et al. Solution-Phase Synthesis of TiO2 nanoparticles and nanocrystals. Chemical Reviews. 114, 9319-9345 (2014). (Year: 2014).*
Office Action dated Apr. 21, 2021 in corresponding Indian Patent Application No. 201927049763, 6 pages.
Office Action dated Jul. 13, 2021 in corresponding Russian Patent Application No. 2019137617/04(074299), with English Translation, 19 pages.
Search Report dated Jul. 12, 2021 in corresponding Russian Patent Application No. 2019137617/04(074299).
Shehata et al., "Preparation and Characterization of Various Interstitial N-Doped TiO$_2$ Catalysts from Different Nitrogen Dopants for the Treatment of Polluted Water", Chemistry and Materials Research, 2016, vol. 8, No. 6, ISSN 2225-0956 (Online), 11 pages.
Kolesnik, Irina Valerevna, "Dioxide-Based Mesoporous Materials Titan", Thesis for Chemical Sciences degree, Moscow State University of the Lomonosov Moscow State University, 2010, with English Translation of expanded abstract, 19 pages.
Fakhrutdinova, Elena, "Production and Study of Physical and Chemical Properties of Doped Photocatalytic Materials Based on Titanium Dioxide", Thesis for Doctor of Chemical Sciences degree, National Research Tomsk Polytechnic Institute of Higher Education State University, 2014, with English Translation of expanded abstract, 32 pages.

* cited by examiner

*Primary Examiner* — Sheng H Davis
(74) *Attorney, Agent, or Firm* — Wenderoth, Lind & Ponack, L.L.P.

(57) ABSTRACT

A nano-functionalized support comprises an application surface and a photocatalytic nanoparticle coating deposited on the application surface. The photocatalytic nanoparticle coating comprises titanium dioxide doped with a nitrogen-containing doping agent.

4 Claims, 5 Drawing Sheets

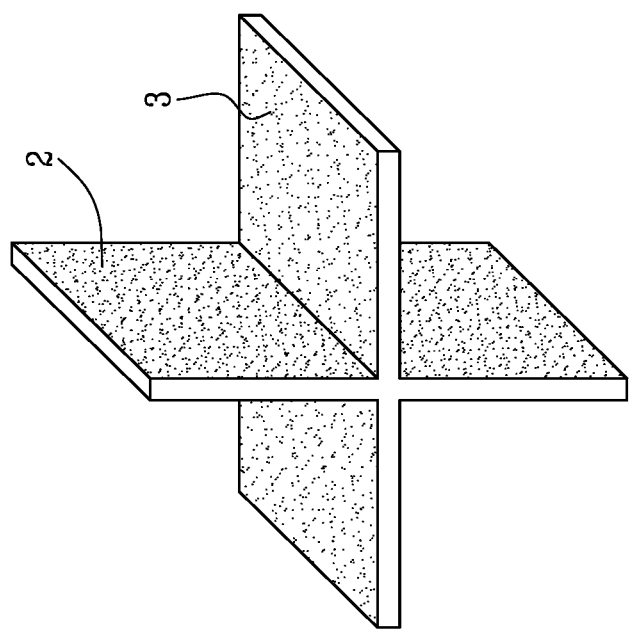
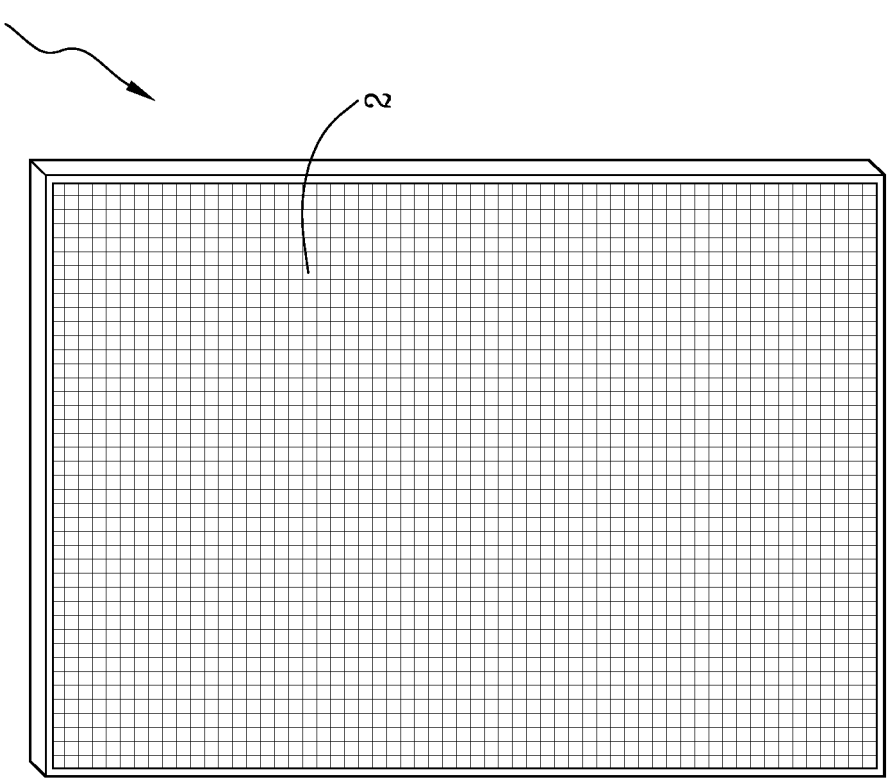

NANO-FUNCTIONALIZED SUPPORT AND PRODUCTION METHOD THEREOF

FIELD OF THE INVENTION

The present invention concerns the sector of devices for reducing polluting agents in a gaseous mixture.

In particular, the present invention concerns a nano-functionalized support which is particularly suitable for installation in an air filter.

BACKGROUND OF THE INVENTION

The development and spread of human activities over the years has led to an increasingly significant increase in polluting substances present in the air that we breathe.

In particular, attention is increasingly focused on the effects that the emission of the pollutants produced—for example by production systems and means of transport—has on the environment and ecosystems.

However, many studies have demonstrated that the level of pollutants that accumulate in a closed area can be equal to, or even greater than, the level present in the outside environment.

The substances present at the highest levels are generally nitrogen oxides ($NO_x$) and volatile organic compounds (VOCs), which can also originate from commonly used domestic objects, including: cleaning products, deodorants, air conditioning systems and interior furnishings.

The need to ensure the livability of indoor, domestic or work environments, without the health of the occupants being jeopardized, has led to the study of filtering systems that are capable of removing all substances that could be harmful to human health, or at least capable of making these substances innocuous.

In particular, it is known that in the presence of oxygen and water, photocatalytic compounds such as titanium dioxide are capable of efficiently breaking down and oxidizing and above-mentioned pollutant compounds present in the air.

This characteristic is what has led to titanium dioxide becoming a compound that is used particularly in the air filter production sector, since it is capable of markedly improving the quality of the air breathed in domestic and work environments.

In particular, the anatase form of titanium dioxide remains the most promising photocatalytically active semiconductor in this sector and numerous efforts have been made to attempt to optimize the processes for the production and application of this particular crystalline form.

For example, excellent results for this sector have been obtained using a method for the production of an aqueous dispersion of nanoparticles of titanium dioxide in accordance with that which is disclosed in document WO2007088151 by the same applicant.

In further detail, titanium dioxide has photocatalytic properties that can be activated when the compound is illuminated with ultraviolet light, for example with a wavelength ranging between 300 and 390 nm, and therefore only 5% of the visible light radiation is able to activate it.

The incident photons are absorbed by the titanium dioxide, giving rise to the formation of radicals that are capable of oxidizing many environmental contaminants, thus making them innocuous.

It follows that this type of device has a very low level of efficiency unless it is used in combination with ultraviolet lamps specially designed and produced to carry out the function of activating the titanium dioxide.

Over the course of the last decades, the problem of the lack of absorption of visible radiation has been solved by using doping agents that are capable of improving the photocatalytic efficiency of $TiO_2$ in the visible region. Some doping agents that have been studied are for example the noble metals, the rare-earth elements, several transition metals (Cu, Ni, Co, Mn, Fe, Cr etc.) and non-metals (such as C, S, F and N). In particular, interesting results have been obtained by using $TiO_2$ doped with nitrogen, which modifies the band gap energy of titanium dioxide, increasing its photocatalytic efficiency in the visible region.

An example concerning photocatalytic application of nitrogen-doped titanium dioxide in the visible region appears in the article by M. Tahir et. al. (M. Tahir, B. Tahir, Applied Surface Science 377 (2016) 244-252), in which a ceramic support with a honeycomb structure and that is coated with nitrogen-doped $TiO_2$ is described. However, this coated support was used exclusively to study the efficiency of photocatalytic reduction of $CO_2$ to CO and $CH_4$, under visible light irradiation, in the presence of molecular hydrogen, while applications concerning oxidation (also carried out in the visible region) of polluting agents such as nitrogen oxides (NO, $NO_x$, $NO_2$) and volatile organic compounds (VOCs) are not described.

Moreover, the process for preparing the coated support described in the article by M. Tahir et al. does not make it possible to obtain a product that can be used on an industrial scale. In fact, by applying the process described in this article, one obtains a support coated with a considerable amount of loose, doped $TiO_2$ powder not adhering to the surface. This limits the possibility of its incorporation in a device for water and air treatment and thus its use on a large scale. In fact, as highlighted in the comparative experiment described in the section of examples, the support coated according to the process described by M. Tahir et al. requires a washing step prior to its use in order to eliminate the doped titanium dioxide powder not adhering to the surface, resulting in considerable losses and waste of the product. Furthermore, the washed support reveals reduced photocatalytic efficiency in terms of oxidation of polluting agents (particularly nitrogen oxides) in the visible region.

In this context, the technical task underlying the present invention is to propose a nano-functionalized support that can be subsequently installed inside an air filter and that overcomes at least some of the drawbacks of the prior art cited herein above.

SUMMARY OF THE INVENTION

The defined technical task and the specified aims are substantially achieved by a nano-functionalized support comprising the technical characteristics set forth in one or more of the appended claims.

In accordance with the present invention, a nano-functionalized support is shown which comprises an application surface configured to receive nanoparticles and a photocatalytic nanoparticle coating deposited on the application surface.

The photocatalytic nanoparticle coating comprises titanium dioxide doped with a nitrogen-containing doping agent.

BRIEF DESCRIPTION OF THE FIGURES

Further characteristics and advantages of the present invention will become more apparent from the indicative and thus non-limiting description of a preferred, but not exclusive, embodiment of a nano-functionalized support, as illustrated in the accompanying drawings, of which:

FIG. 1 shows a nano-functionalized support according to the present invention;

FIG. 2 shows a detail of a nano-functionalized support;

In FIG. 1, a nano-functionalized support that is installable for example inside an air filter is indicated in general by the number 1.

DETAILED DESCRIPTION OF THE INVENTION

Figure 3:
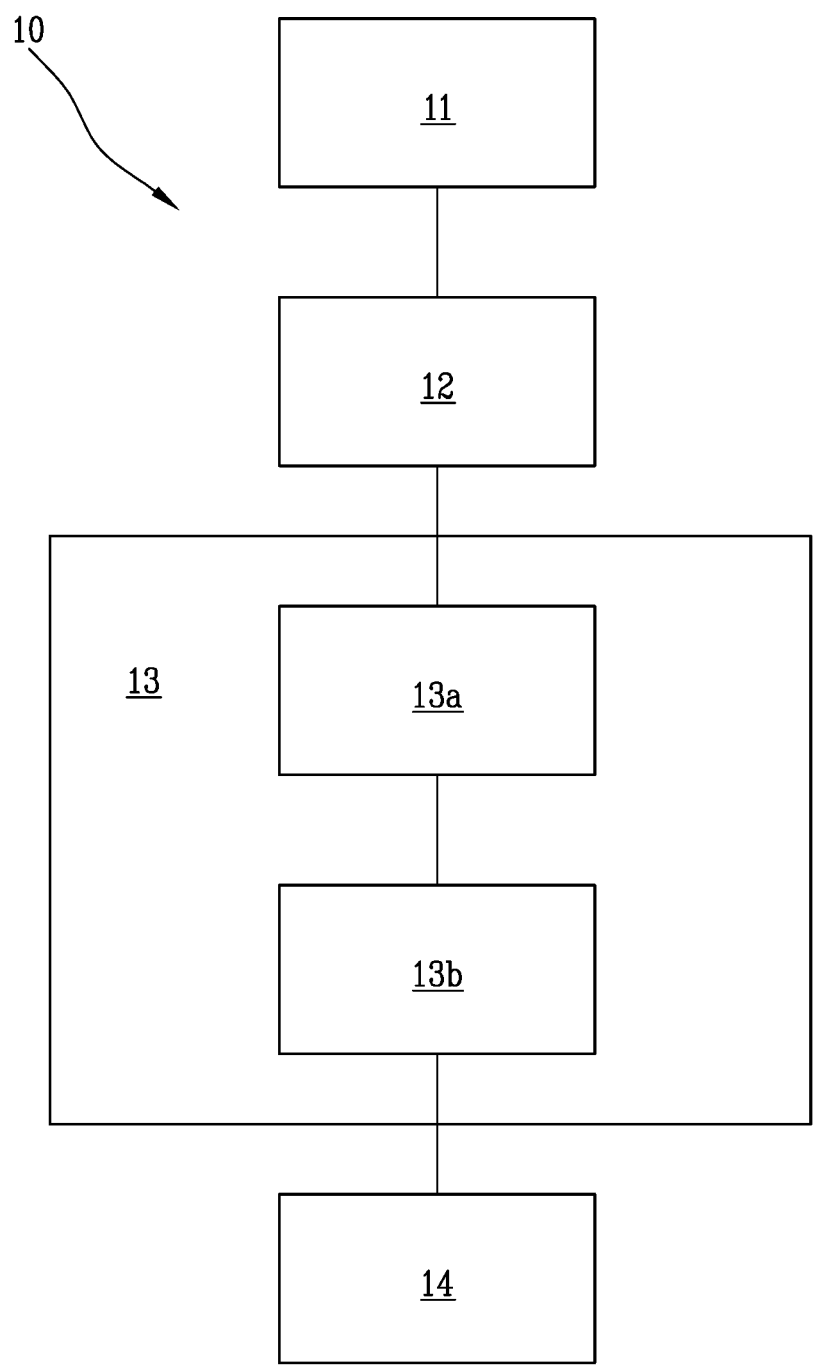
FIG. 3 is a block diagram of a method for producing a nano-functionalized support.

The term nano-functionalized is used to indicate that the support has a coated surface, preferably homogeneously coated, with nanoparticles that have photocatalytic properties which are suitable for facilitating the degradation of polluting substances, principally by means of oxidation processes.

The support 1 comprises an application surface 2 and a photocatalytic nanoparticle coating 3 configured to be deposited on the application surface 2.

The nanoparticle coating 3 is realized by deposition of a suspension of photocatalytically active nanoparticles, preferably comprising nanoparticles of titanium dioxide doped with nitrogen, in which the nanoparticles are in the anatase crystalline form.

Prior to application to the support 1, the nanoparticle coating 3 is doped by means of a nitrogen-containing doping agent.

In other words, the application surface 2 is coated with titanium dioxide in the form of nanoparticles doped with nitrogen.

In particular, the precursor utilized as the nitrogen-containing doping agent is preferably selected from among: amines, amides, organic ammonium salts and inorganic ammonium salts.

The presence of nitrogen makes it possible to modify the band gap energy of the titanium dioxide, specifically to reduce it, making its photocatalytic properties activatable using a broad range of the visible light spectrum and not only with the very limited ultraviolet component as takes place for example in devices of the prior art.

Preferably, the application surface 2 is made of a ceramic material, which proves to be particularly suitable in that it provides an inert and very resistant support, thus ensuring long lifetimes for the devices in which it is used.

Even more preferably, the application surface is realized using at least one of: cordierite, mullite and/or alumina.

For the purpose of ensuring optimal filtering results and maximizing the efficiency of the support 1, the application surface 2 is realized by means of a matrix with thin ceramic walls that define a honeycomb structure constituted by a plurality of parallel channels that are open at both ends so as to enable the passage of a gaseous mixture. This honeycomb application surface (also called the honeycomb surface) is characterized by a CSPI (cells per square inch) value of 40 to 120, preferably 50 to 100, more preferably 50 to 70, even more preferably 55 to 65. In other words, the application surface 2 has a plurality of channels, each of which is coated with a nanoparticle coating 3, thus defining a plurality of oxidation sites in which, by means of the activation of the photocatalytic properties of the titanium dioxide nanoparticles doped with a nitrogen-containing doping agent, on the part of an incident photon, the environmental pollutants are adsorbed and degraded, obtaining purification of the gaseous mixture, particularly air, passing through the channels of the application surface 2.

For example, the nitrogen oxides undergo degradation to nitrates, whereas other volatile organic substances are oxidized forming carbon residues and/or carbon dioxide.

The sub-products resulting from filtration of the air can easily be washed away from the application surface 2, completely restoring the operating state thereof.

The nano-functionalized support 1 of the present invention thus proves to be particularly suited to incorporation in a device for abating polluting agents in a gaseous mixture such as air for example.

A method 10 for producing a nano-functionalized support 1 according to that which is described hereinabove also constitutes an object of the present invention.

The method 10 comprises the steps of: synthesizing 11 an aqueous suspension of nanoparticles of titanium dioxide; adding 12 a nitrogen-containing doping agent to the suspension, realizing a suspension of nanoparticles and the nitrogen-containing doping agent; applying 13 the suspension to the application surface 2, realizing a nano-functionalized support 1; subjecting 14 the support 1 to a heating cycle.

Preferably, in step 11, the aqueous suspension of the nanoparticles of titanium dioxide in anatase form is prepared according to that which is disclosed in patent WO2007088151. In particular, a titanium alkoxide is made to react under heat in water in the presence of a mineral acid and a non-ionic surfactant.

The starting material for the synthesis of the aqueous suspension of nanoparticles of titanium dioxide in anatase form is chosen from the substances of the group of titanium alkoxides. In particular, the alkoxide can be selected from among titanium methoxide, titanium ethoxide, titanium normal-propoxide, titanium isopropoxide, titanium normal-butoxide, and titanium isobutoxide. In a preferred embodiment, the titanium alkoxide selected is titanium isopropoxide (TIP) as it is less expensive and reacts more efficiently under the reaction conditions of the present synthesis.

Examples of non-ionic surfactants that can be used are: non-ionizable ethers, esters and ether esters. The use of Triton X-100 (TX-100) is particularly preferred for the present synthesis.

Mineral acid means an acid selected from among: hydrochloric acid, nitric acid, sulphuric acid, perchloric acid, hydrobromic acid and hydrogen iodide. In a preferred embodiment, the mineral acid used is selected from among hydrohalic acids, particularly hydrochloric acid.

The titanium alkoxide/mineral acid molar ratio is in the range of 0.005 to 15, preferably 5 to 6.

The reaction temperature ranges between 15 and 95° C., preferably between 45 and 55° C., and the reaction time ranges between 12 and 72 hours, and it is preferably equal to 24 hours.

The product obtained is an aqueous suspension of $TiO_2$ nanoparticles in the anatase phase with sizes ranging between 30 and 50 nm measured with methods known in the sector, such as FEG-SEM (Field Emission Gun Scanning Electron Microscopy), TEM (Transmission Electron Microscopy) and DLS (Dynamic Light Scattering). The polydispersity index of the nanoparticles, as measured with the DLS technique, is lower than 0.3, preferably ranging between 0.21 and 0.29, and more preferably between 0.216 and 0.286. The concentration of $TiO_2$ nanoparticles suspended in water ranges between 1 and 10% by weight, preferably between 2 and 8% by weight.

The suspension of nanoparticles is stable for very long periods of time without the appearance of coagulation and conglomeration phenomena. Subsequently, in step 12, a nitrogen-containing doping agent is added to said aqueous suspension of titanium dioxide nanoparticles, said nitrogen-containing doping agent being suitably selected from among: amines, amides, organic ammonium salts and inorganic ammonium salts.

Some possible operating parameters for realizing the doped suspension are reported below by way of non-limiting example.

Example A: 5.00 g of concentrated hydrochloric acid, 7.50 g of TX-100 and water, for a total of 750.00 g, are mixed in a 2-litre reactor and heated to 50° C. 50.00 g of titanium isopropoxide (TIP) are added and the formation of a white precipitate is observed. A stable transparent sol of titanium dioxide is formed after 24 hours.

Example B: 97.81 g of an aqueous suspension of titanium dioxide obtained as described for Example A and 2.00 g of diethanolamine are mixed in a 200 ml beaker, the temperature is set at 25° C., and after eighteen hours of mixing an opalescent white solution is obtained with a 5.87% reduction by weight of titanium dioxide and 0.27% reduction by weight of nitrogen.

Example C: 97.00 g of an aqueous suspension of titanium dioxide obtained as described for Example A and 4.07 g of diammonium citrate are mixed in a 200 ml beaker, the temperature is set at 25° C., and after twenty-four hours of mixing an opalescent white solution is formed with a 5.76% reduction by weight of titanium dioxide and a 0.49% reduction by weight of nitrogen.

Example D: 90.0 g of the suspension obtained as described for Example C were applied with the flow-coating technique on a 150×150×20 cm support of ceramic material with a honeycomb structure. Said procedure comprises the application of the suspension on the support, said suspension being drawn from a tank by a pump and said support being positioned above a rack so that the excess material can be collected and reused.

The support thus prepared was subjected to a firing cycle in a continuous electric furnace at 500° C. for three hours with the belt speed set at 4 m/h. After firing, the amount of doped titanium dioxide deposited was equal to 5.8 g. A sample with dimensions of 77×77×20 cm was obtained from this support and a pollutant abatement test (for NO, $No_x$, $NO_2$) was carried out with this sample (see FIG. 4), using a COOL WHITE LED with a power of 25 W as the light source.

Example E: 97.00 g of an aqueous suspension of titanium dioxide obtained as described for Example A and 4.00 g of tetrabutylammonium hydroxide are mixed in a 200 ml beaker and the temperature is set at 25° C.; after twenty-four hours of mixing an opalescent white solution is formed with a 5.76% reduction by weight of titanium dioxide and a 0.085% reduction by weight of nitrogen.

Example F: 97.00 g of an aqueous suspension of titanium dioxide obtained as described for Example A and 6.00 g of tetrabutylammonium hydroxide are mixed in a 200 ml beaker and the temperature is set at 25° C.; after twenty-four hours of mixing an opalescent white solution is formed with a 5.65% reduction by weight of titanium dioxide and a 0.125% reduction by weight of nitrogen.

Example G: 49.49 g of an aqueous suspension of titanium dioxide obtained as described for Example A and 0.53 g of urea are mixed in a 200 ml beaker and the temperature is set at 25° C.; after twenty-four hours of mixing an opalescent white solution is formed with a 5.93% reduction by weight of titanium dioxide and a 0.498% reduction by weight of nitrogen.

Example H: 49.49 g of an aqueous suspension of titanium dioxide obtained as described for Example A and 1.06 g of urea are mixed in a 200 ml beaker; the temperature is set at 25 C and after one hour of mixing an opalescent white solution is formed with a 5.87% reduction by weight of titanium dioxide and a 0.980% reduction by weight of nitrogen.

Example I: 86.21 g of an aqueous suspension of titanium dioxide obtained as described for Example A and 13.79 g of triethanolamine are mixed in a 200 ml beaker; the temperature is set at 25° C. and after four hours of mixing an opalescent white solution is formed with a 5.17% reduction by weight of titanium dioxide and a 1.29% reduction by weight of nitrogen.

Example L: 125.0 g of the suspension obtained as described for Example I were applied with the flow-coating technique on a 150×150×20 cm support of ceramic material with a honeycomb structure. Said procedure comprises the application of the suspension on the support, said suspension being drawn from a tank by a pump and said support being positioned above a rack so that the excess material can be collected and reused.

Figure 5:
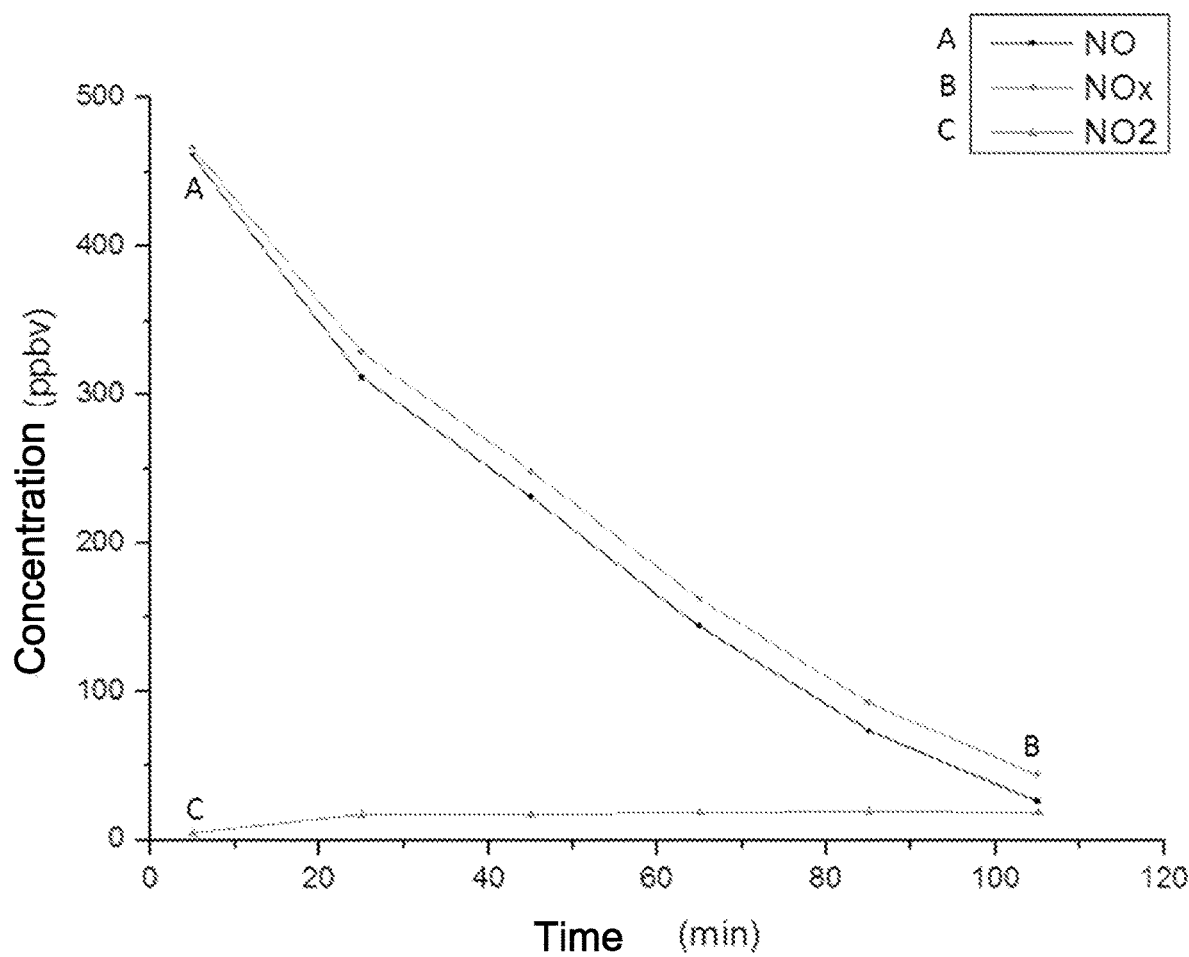
FIG. 5 is a graph showing the abatement trend for the polluting agents (NO, $NO_x$, $NO_2$) by means of irradiation of the sample prepared as per Example L, said irradiation being performed with a COOL WHITE LED with a power of 25 W.

The support thus prepared was subjected to a firing cycle in a continuous electric furnace at 500° C. for 3 hours with the belt speed set at 4 m/h. After firing, the amount of doped titanium dioxide deposited was equal to 8.2 g. A sample with dimensions of 77×77×20 cm was obtained from this support and a pollutant abatement test (for NO, $NO_x$, $NO_2$), shown in FIG. 5, was carried out with this sample, using a COOL WHITE LED with a power of 25 W as the light source.

Example M (Comparative Experiment):

A $TiO_2$ sol containing urea as a source of nitrogen was synthesized by accurately reproducing the steps described in section 2.1 of the paper by M. Tahir et al. (M.Tahir, B. Tahir, Applied Surface Science 377 (2016) 244-252). By means of the flow-coating technique, said sol was then applied onto a 150×150×20 cm support of ceramic material with a honeycomb structure. The support thus prepared was subjected to a firing cycle in a continuous electric furnace at 500° C. for 3 hours with the belt speed set at 4 m/h. After firing, the amount of doped titanium dioxide deposited was equal to 2. However, following this step, a problem was found concerning the presence of a considerable amount of loose, doped titanium dioxide powder not adhering to the surface of the support.

For this reason, prior to the analysis, washing with water had to be carried out so as to eliminate the loose powder and prevent it from spreading into the environment (which is potentially hazardous for the health of operators), as well as to ensure better handleability of the support. The washing procedure led to the elimination of a large amount of non-adherent doped titanium dioxide powder resulting in considerable losses and waste of the product. A sample with dimensions of 77×77×20 cm was obtained from this washed support and a pollutant abatement test (for NO, $NO_x$, $NO_2$) was carried out with this sample (see FIG. 6), using a COOL WHITE LED with a power of 25 W as the light source.

Figure 4:
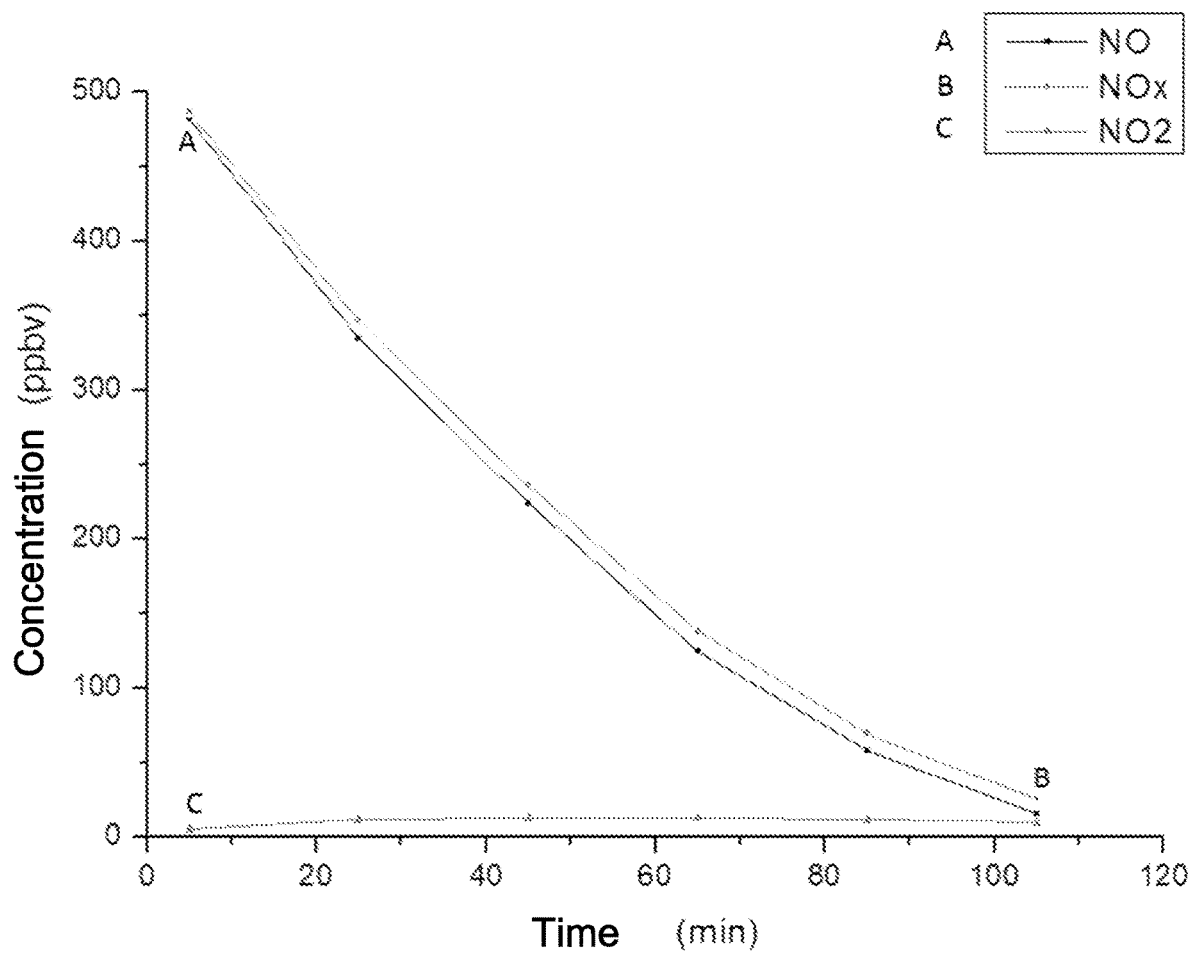
FIG. 4 is a graph showing the abatement trend for the polluting agents (NO, $NO_x$, $NO_2$) by means of irradiation of the sample prepared as per Example D, said irradiation being performed with a COOL WHITE LED with a power of 25 W.
Figure 6:
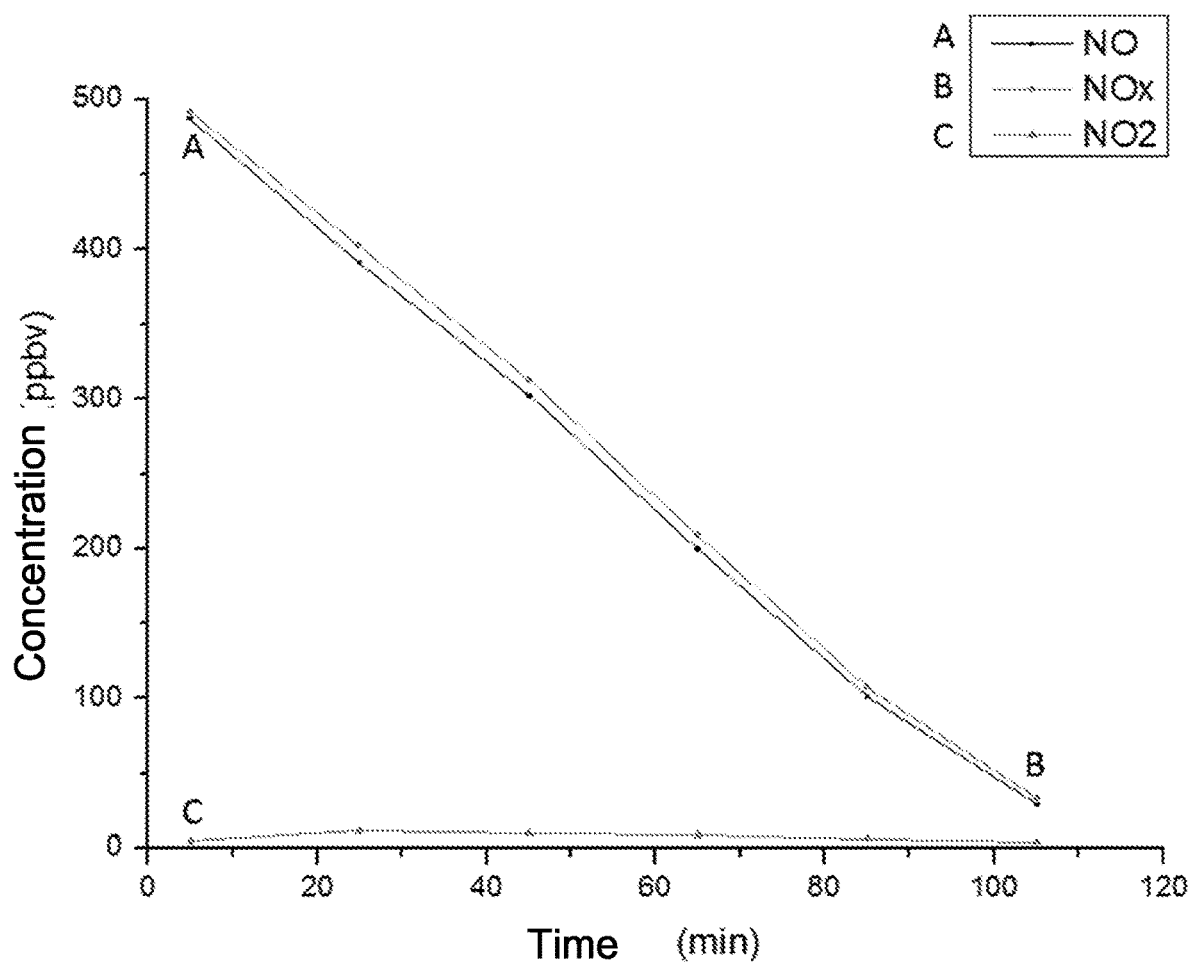
FIG. 6 is a graph showing the abatement trend for the polluting agents (NO, $NO_x$, $NO_2$) by means of irradiation of the sample prepared by accurately following the process of the prior art as described for Example M, said irradiation being performed with a COOL WHITE LED with a power of 25 W.

These results were compared with the results obtained with the nano-functionalized support of the present invention obtained as described for Example D, shown in FIG. 4. The graph showing the trend for the polluting agents in FIG. 6 shows a convex trend and not a concave trend as in the case of the graph in FIG. 4. It can thus be noted from the comparison of the curves in the two graphs that the photocatalytic efficiency of the washed support obtained according to the process of the prior art proves to be weaker than that of the support of the present invention. In fact, in the case of the support obtained with the prior-art process, after 50 minutes of irradiation, the concentration of NO and $NO_x$ is around the level of 300 ppbv, whereas in the case of the nano-functionalized support of the present invention, the concentration proves to be around the level of 200 ppbv.

The application step 13 comprises a first substep of applying 13a the suspension of nanoparticles of titanium dioxide and nitrogen-containing doping agent to the application surface 2, for example by means of a spraying process, and a second substep of applying 13b a flow of compressed air on the application surface 2 so as to remove excess deposited nanoparticle coating 3.

Alternatively, the doped suspension can be applied by means of dip coating or flow coating processes, or applications typical of the ceramics field such as veil-glazing, screen printing, bell-glazing, air brushing or digital injection.

In particular, after the support 1 has rested for a period of time, the heating cycle in the step of subjecting 14 the support 1 to a heating cycle is carried out, heating it to a temperature between 490° C. and 510° C. During the heating cycle (also called the calcination step), the doping of the titanium dioxide with nitrogen from the nitrogen-containing doping agent takes place. Doping of the $TiO_2$ with nitrogen takes place during the calcination step and the nitrogen penetrates the $TiO_2$ nanoparticles, positioning itself in a substitutional position inside the $TiO_2$ lattice and/or in an interstitial position, that is, inside the crystalline planes of $TiO_2$ lattice. In the case in which a static furnace is used, the heating cycle is preferably carried out with a temperature variation coefficient of 50° C./h for a period of ten hours, reaching a maximum temperature of about 500° C. However, in the case in which a continuous run furnace is used, a 3-hour heating cycle can be implemented, with a preheating step, a 500° C. heating step and a cooling step, with a running speed of about 4 m/h.

In general, it can be noted that the heating cycle is of a duration substantially ranging from 2 to 11 hours, depending on the type of heating device used.

A further object of the present invention is a method for the abatement of polluting agents in a gaseous mixture, starting with a step of arranging a device for abating polluting agents, said device comprising at least one nano-functionalized support 1, in accordance with that which is disclosed above, and possibly a light source of visible light.

The method further comprises subjecting the device to a flow of a gaseous mixture and illuminating the at least one nano-functionalized support 1 by means of a beam of visible light.

By illuminating the support, the photocatalytic properties of the nanoparticle coating 3 present on the application surface can be activated. Owing to the particular production method used to produce the support 1, the photocatalytic properties of titanium dioxide prove to be activated by a broad range of wavelengths in the visible light spectrum and not only by the component of the ultraviolet region of the spectrum.

Therefore, when the flow of air travels through the nano-functionalized structure 1, the polluting agents contained in it are oxidized, thereby obtaining an improvement in the quality of the air exiting the device.

Advantageously, the particular method for producing a nano-functionalized support 1 makes it possible to achieve optimal doping of titanium dioxide. Furthermore, the presence of nitrogen ensures activation of the photocatalytic properties of the titanium dioxide nanoparticles also with photons having wavelengths in the visible light region, thereby making it possible to maximize the photocatalytic activity of the nano-functionalized support 1.

The invention claimed is:

1. A method for producing a nano-functionalized support and comprising the steps of:
    synthesizing an aqueous suspension of nanoparticles of titanium dioxide in anatase form with a size ranging between 30 and 50 nm, by reacting a titanium alkoxide in water in the presence of a mineral acid and a non-ionic surfactant at a temperature between 45 and 55° C. for a reaction time between 12 and 72 hours;
    adding a nitrogen-containing doping agent to the suspension, producing a suspension of nanoparticles and the nitrogen-containing doping agent, wherein said nitrogen-containing doping agent is selected from the group consisting of: diethanolamine, diammonium citrate, tetrabutylammonium hydroxide and triethanolamine;
    applying said suspension, forming a photocatalytic nanoparticle coating, to an application surface, producing a nano-functionalized support, wherein said application surface has a honeycomb structure;
    subjecting said nano-functionalized support to a heating cycle.

2. The method according to claim 1, wherein said step of applying said suspension to an application surface comprises the substeps of:
    spraying said doped suspension on said application surface;
    applying a flow of compressed air on the application surface, thereby facilitating the removal of an excess part of the suspension from the application surface.

3. The method according to claim 1, wherein the heating cycle is carried out by heating the nano-functionalized support to a temperature between 490° C. and 510° C.

4. The method according to claim 1, wherein the heating cycle is of a duration ranging from 2 to 11 hours.

* * * * *